(12) United States Patent
Crowley et al.

(10) Patent No.: US 9,260,695 B2
(45) Date of Patent: *Feb. 16, 2016

(54) PROCESS FOR CELL CULTURING BY CONTINUOUS PERFUSION

(71) Applicant: DPx Holdings B.V., Farmingham, MA (US)

(72) Inventors: John Crowley, Dublin (IE); Maike Wubben, Groningan (NL); Jose Manuel Coco Martin, Roden (NL)

(73) Assignee: DPX Holdings B.V., Farmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,878

(22) Filed: Oct. 14, 2013

(65) Prior Publication Data

US 2014/0087424 A1    Mar. 27, 2014

Related U.S. Application Data

(63) Continuation of application No. 13/478,307, filed on May 23, 2012, and a continuation of application No. 10/591,118, filed as application No. PCT/EP2005/002374 on Mar. 4, 2005, now Pat. No. 8,206,981.

(30) Foreign Application Priority Data

| Mar. 5, 2004 | (EP) | .................................... | 04075702 |
| Mar. 5, 2004 | (EP) | .................................... | 04075703 |
| Sep. 27, 2004 | (EP) | .................................... | 04077656 |
| Sep. 27, 2004 | (EP) | .................................... | 04077657 |

(51) Int. Cl.
  *C12N 5/02* (2006.01)
  *C12N 5/079* (2010.01)
  (Continued)

(52) U.S. Cl.
  CPC ............. *C12N 5/0621* (2013.01); *C07K 16/00* (2013.01); *C12M 25/10* (2013.01); *C12M 29/10* (2013.01);
  (Continued)

(58) Field of Classification Search
  None
  See application file for complete search history.

(56) References Cited

U.S. PATENT DOCUMENTS

| 4,806,484 A | 2/1989 | Petrossian et al. |
| 5,019,512 A | 5/1991 | Varecka et al. |

(Continued)

FOREIGN PATENT DOCUMENTS

| CA | 2252972 | 5/2000 |
| CA | 2351156 | 1/2003 |

(Continued)

OTHER PUBLICATIONS

Mercille, et al. (2004) Biotechnology and Bioengineering, 43(9): 833-846.

(Continued)

*Primary Examiner* — Sharmila G. Landau
*Assistant Examiner* — Stephanie McNeil
(74) *Attorney, Agent, or Firm* — McDonnell Boehnen Hulbert & Berghoff LLP (57) ABSTRACT

The invention relates to a process for the culturing of cells by continuous perfusion culturing of a cell culture comprising cell culture medium and cells, wherein cell culture medium is added to the cell culture, the cell culture is circulated over a filter module comprising hollow fibers resulting in an outflow of liquid having a lower cell density than the cell culture and the flow within the filter module is an alternating tangential flow. Preferably, culture medium is added at a particular perfusion rate and/or biomass is removed form the culture at least once. The method is especially suitable for the culturing of aggregating cells. The invention also relates to such a process wherein a biological substance, preferably an antibody, is produced by the cells, which biological substance may be further purified in downstream processing.

20 Claims, 8 Drawing Sheets (51) Int. Cl.

| | |
|---|---|
| C12M 1/12 | (2006.01) |
| C12M 1/00 | (2006.01) |
| C12N 5/00 | (2006.01) |
| C12N 5/071 | (2010.01) |
| C12P 19/34 | (2006.01) |
| C12P 21/00 | (2006.01) |
| C07K 16/00 | (2006.01) |

(52) U.S. Cl.
CPC ............... *C12N 5/00* (2013.01); *C12N 5/0602* (2013.01); *C12P 19/34* (2013.01); *C12P 21/00* (2013.01); *C07K 2317/14* (2013.01); *C12N 2521/00* (2013.01)

(56) References Cited

U.S. PATENT DOCUMENTS

| | | |
|---|---|---|
| 5,256,294 A | 10/1993 | van Reis |
| 5,286,646 A | 2/1994 | Kearns et al. |
| 5,595,909 A | 1/1997 | Hu et al. |
| 5,871,999 A | 2/1999 | Boraston |
| 6,001,585 A | 12/1999 | Gramer |
| 6,103,526 A | 8/2000 | Smith et al. |
| 6,168,941 B1 | 1/2001 | Liu et al. |
| 6,544,424 B1 | 4/2003 | Shevitz |
| 6,855,544 B1 | 2/2005 | Hateboer et al. |
| 2003/0054544 A1 | 3/2003 | Gruenberg |
| 2003/0134388 A1 | 7/2003 | Sasaki et al. |
| 2004/0014711 A1 | 1/2004 | Endo et al. |
| 2006/0014239 A1 | 1/2006 | Luttmann et al. |

FOREIGN PATENT DOCUMENTS

| | | |
|---|---|---|
| DE | 10120835 | 11/2002 |
| EP | 0317874 | 5/1989 |
| EP | 0343635 | 11/1989 |
| EP | 362408 | 4/1990 |
| EP | 1354943 | 10/2003 |
| EP | 1157098 | 9/2008 |
| JP | 61199788 | 9/1986 |
| JP | 6485068 | 3/1989 |
| JP | 05-153973 | 6/1993 |
| JP | 2001-149099 | 6/2001 |
| JP | 2002-020282 | 1/2002 |
| JP | 2002-113896 | 4/2002 |
| JP | 2003-219873 | 8/2003 |
| JP | 2005-041984 | 2/2005 |
| JP | 2008-308560 | 12/2008 |
| WO | 88/00614 | 1/1988 |
| WO | 9305145 | 3/1993 |
| WO | 96/34117 | 10/1996 |
| WO | 00/46354 | 1/2000 |
| WO | 00/44883 | 8/2000 |
| WO | 00/63403 | 10/2000 |
| WO | 01/38362 | 5/2001 |
| WO | 01/51616 | 7/2001 |
| WO | 03025158 | 3/2003 |
| WO | 2004099396 | 11/2004 |
| WO | 2005095578 | 10/2005 |
| WO | 2008006494 | 1/2008 |

OTHER PUBLICATIONS

Kruse, et al., (1965) The Journal of Cell Biology, 27: 273-279.
Jordan, et al, (1992)"Tuning of shear sensitivity of CHO cells and its correlation with the size distribution of cell aggregates" in Animal cell technology: developments, processes and products, eds. Spier, R.E., Griffiths, J.B. and MacDonald, C. London: Butteworth-Heinemann, pp. 418-420.
Snabre, et al., (1987) Biophys. J., 51: 795-807.
Moreira, et al., (1992) "Aggregate suspension cultures of BHK cells" in Animal cell technology: developments, processes and products, eds. Spier, R.E., Griffiths, J.B. and MacDonald, C. London: Butteworth-Heinemann, pp. 411-413.
Maiorella, et al., (1991) Biotechnol. Bioeng., 37(2): 121-126.
A/G Technology Corporation, "Operating Guide" Jan. 1999, NG Technology Corporation.
Yun-Seung Kyung, et al., (1994) Cytotechnology, 14: 183-190.
Anthony S. Lubiniecki, "Large-scale mammalian cell culture technology", CRC Press, 1990, pp. 237-240.
Gary C. Howard, et al., "Basic Methods in Antibody Production and Characterization", CRC Press, 2000, p. 91.
Michael A. Winkler, "Chemical engineering problems in biotechnology", Published by Springer, 1990, pp. 329-330.
Terence Cartwright, "Animal cells as bioreactors", Cambridge University Press, 1994, pp. 72-86.
Shepherd, et al.,"Monoclonal antibodies: a practical approach", Oxford University Press, 2000, pp. 137-138.
Maureen Anne Harrison and Ian Fraser Rae, "General techniques of cell culture", Cambridge University Press, 1997, p. 128.
E.C. Beuvery, et al.,"Animal Cell Technology: Developments Towards the 21st Century", Springer, 1995, p. 554.
Jerry Shevitz, et al, "Stirred tank perfusion reactors for cell propagation and monoclonal antibody production" in "Advances in Biotechnological Processes" (1989), Alan R. Liss, Inc., Chapter 11, pp. 81-106.
Jones, D. et al., (2003) Biotechnol. Prog. 19: 163-168.
Fallaux et al., (1998). Hum Gene Ther. 9(13): 1909-17.
Furey, J. "Continuous and Scalable Production from a Bioreactor" Poster presentation at the Cell Culture Engineering VII conference, Snowmass Village, Colorado, United States of America, Apr. 1-6, 2002.
Furey, J. (2002) Genetic Engineering News, 22(7): 62-63.
Bleckwenn, N.A., Bentley, W. And Shiloach, J. "Production and Glycosylation Analysis of Model proteins from Vaccinia Virus-Mammalian Expression System", poster presentation at the 18th meeting of the European Society for Animal Cell technology (ESACT), Granada, Spain, May 11-14, 2003.
Bleckwenn N.A. et al., "Scalable Protein Production in Anchorage Dependent Mammalian Cells", poster presentation at Bioscience day conference, 2003.
Bleckwenn N.A. et al., entitled "Expression of EGPF Reporter protein with a Recombinant Vaccinia Virus—Comparison of Microcarrier and Cell Susupension Based Bioreactor Systems" poster presentation at meeting of the American Chemical Society, 2003.
Press release: "Scalable and Reliable Perfusion—Is It Really Possible?" published in the United Kingdom, Apr. 17, 2002.
Jackson, L.R., Trudel. L.J., Fox, J.G. and Lipman, N.S. (1996) "Evaluation of hollow fibre bioreactors as an alternative to murine ascites production for small scale monoclonal antibody production" Journal of Immunological Methods, 189, pp. 217-231.
Piret, J.M. and Cooney, C.L. (1990) "Mammalian cell and protein distributions in ultrafiltration hollow fibre bioreactors" Biotechnology and bioengineering, 36, pp. 902-910.
Falkenberg, F.W., Weichert, H. Krane, M., Bartels, I., Palme, M., Nagels, H.-O. and Feibig, H. (1995) "In vitro production of monoclonal antibodies in high concentration in a new and easy to handle modular minifermenter" Journal of Immunological Methods, 179, pp. 13-29.
Xie, et al., (2002) Biotechnology and Bioengineering, 80(5): 569-579.
Risenberg, et al., (1999) Appl Microbiol Biotechnol, 51:422-430.
Portner, et al., (1995) "Evaluation of Precess Strategies for efficient cultivation of hybridoma cells based on mathematical models," Animal Cell Technology: Developments Towards the 21st Century, Springer, eds. Reuvery, et al., p. 829-831.
Belfort, et al., (1994), "New Development in Membrane Bioreactors," Membrane Processes in Separation and Purification, eds. Crespo and Boddeker, pp. 127-148.
Fuchs, et al., (2002) Jounral of Biotechnology, 93:243-251.
Griffiths (2000), "Immobilized Cultures," Animal Cell Culture: A Practical Approach, Oxford University Press, eds Masters et al., p. 58-67.
Harrison, et al, (1997), General Techniques of cell culture, Cambridge University Press, p. 122-138.

(56) References Cited

OTHER PUBLICATIONS

Horwath, (1995) "Facility Design and Validation Considerations for Continuous Cell Culture Processes," Animal Cell Technology: Developments Towards the 21st Century, Springer, eds. Reuvery, et al., p. 553-559.
Maranga, et al., (2006) Biotechnology and Bioengineering, 94(1): 139-150.
Norris, et al.,(2002) "Growth of Cell Lines in Bioreactors," Basic Methods in Antibody Production and Characterization, CRC Press, eds. Howard, et al., p. 87-103.
Furey, J., "Continuous cell using the ATF system", (2000) Genetic Engineering News, vol. 20(10, 15), pp. 52-53.
Voisard, D., et al., Potential of cell retention techniques for large-scale high-density perfusion culture of suspended mammalian cells., Biotechnology and Bioengineering, (2003), vol. 82(7) pp. 751-765.
Jorjani, P. et al., "Effects of cell density and temperature on oxygen consumption rate for different mammalian cell lines", Biotechnology and Bioengineering (1999), vol. 64(3) pp. 349-356.
Jones, D. H. et al., "Per. C6 cell for human antibody production crucell's technology maintains human glycosylation patterns", Genetic Engineering News, (2002), vol. 22(10) pp. 50-54.
Velez, D. et al., "Use of tangential flow filtration in perfusion propagation of hybridoma cells for production of momocional antibodies", Biotechnology and Bioengineering (1989) vol. 33(7, 20) pp. 938-940.
Woodside S. M. et al., "Mammalian cell retention devices for stirred perfusion bioreactors" Cytotechnology (1998) vol. 28 (1-3) pp. 163-175.
Banik G. G. et al., "Partial and total cell retention in a filtration-based homogeneous perfusion reactor" Biotechnology Prog. (1995) vol. 11, pp. 584-588.
Chisti, Y, Strategies in downstream processing, in: Bioseparation and Bioprocessing: A Handbook (Subramanian, G., editor), Wiley-VCH, New York, pp. 3-30.
John R. W. Masters, Animal Cell Culture: A Practical Approach, Oxford University Press, 2000 ("Masters (2000)"); p. 59.
João C. Crespo, Karl W. Boddeker, North Atlantic Treaty Organization. Scientific Affairs Division, "Membrane processes in separation and purification", Springer, 1994 ("Crespo and Boddeker (1994)"); pp. 135-137.
Konstantinov, K.B. et al. "Control of Long-Term Perfusion Chinese Hanster Ovary Cell Culture by Glucose Auxostat" Biotechnol. Prog. vol. 12, pp. 100-109, 1996.
J. Crowley, M. Wübben, J.M. Coco-Martin: "Process Optimization of the Human Cell Line Per.C6 for the Production of Biopharmaceuticals". Presented at Cell Culture Engineering IX, Mar. 7-14, 2004. Cancun, Mexico.
J. Crowley et al. "Pushing mammalian cells to the limit". In DSM Pharma Focus, Issue 14, Jun. 2004.
EX-CELL VPRO brochure, printed 2010.

Tharmalinham et al. (2008) "Pluronic enhances the robustness and reduces the cell attachment of mammalian cells", Molecular Biotechnology 39: 167-177.
Shevitz et al. (1989) "Stirred tank perfusion reactors for cell rpopagation and monoclonal antibody production" in "Monoclonal antibodeis: Production and Application" Advances in Biotechnological Processes, vol. 11:81-106.
Gibco Adenovirus Expression Medium (AEM) Information sheet. Invitrogen Corporation, 2003.
van Reis et al., (1991) "Industrial scale harvest of proteins from mammalian cell culture by tangential flow filtration" Biotech. Bioengn. 38, 413-422.
Kawahara et al., (1994) "High-density culture of FM-3A cells using a bioreactor with an external tangential flow filtration device" Cytotechnology 14, 61-66.
Cortin et al., (2004) "High titer adenovirus vector production in 293S cell perfusion culture" Biotechnol. Prog. 20, 858-863.
van Reis et al., (2001) "Membrane separations in biotechnology" Cuurent opinion in Biotechnology 12(2), 208-211.
Notice of Opposition to a European Patent for EP1720972 & Opposition Requests, Fact and Arguments, Opponent Isenbruck Bosl Horschler LLP, Oct. 7, 2014.
Notice of Opposition to a European Patent for EP1720972 & Opposition Requests, Fact and Arguments, Opponent Leeming, Oct. 7, 2014.
Notice of Opposition to a European Patent for EP1720972 & Opposition Requests, Fact and Arguments, Opponent Boehringer Ingelheim International GmBH, Oct. 8, 2014.
Lindl, et al. "Zell-und Gewebekultur Einfuhrung in die Grundlagen sowie ausgewahtle Methoden und Anwendungen," Stuttgart/New York: Gustav Fischer Verlag, 1987, pp. 83, 157-158. (Original German and translation).
GEN News Highlights, Genetic Engineering & Biotechnology News, 2010.
Renner, et al., Biotechnology and Bioengineering, 41:188-193, 1993.
Wallner, et al., "Formation and Dissociation of Cell ggregates in Suspension CUltures of Paul's Scarlet Rose," Amer J Bot, 60(3):255-261. 1973.
Refine Technologies Internet Disclosure, printed Jun. 2014.
Nordon, R.E., Shu, A., Camach, F. & Milthorpe, B.K. "Hollow-fiber assay for Ligand Mediated Cell Adhesion", Cytometry Part A, 57A: 39-44 (2004).
Card, C. "Metabolically designed Serum-Free Media for HEK293 and PER.C6® Cell Lines", Art to Science, vol. 22, No. 1, 155-157 (2003).
Notice of Opposition to a European Patent for EP1720972 & Opposition Requests, Fact and Arguments, Opponent Toray Industries, Inc., Oct. 7, 2014.
Press Release DS/Crucell, Sep. 23, 2010.
Refine Technology Operating Manuel Version 1.01, 2000.
BioProcess International, Refine Technology, slide show, 2010.
GEN News Highlights. Sep. 23, 2010.
Summons to Oral Proceedings and Preliminary Opinion of the Opposition Division in the Opposition Proceeding involving the European patent, EP1720972B1, mailed Dec. 11, 2015.

PROCESS FOR CELL CULTURING BY CONTINUOUS PERFUSION

The present invention relates to perfusion culturing of cells.

The present invention discloses a process for the culturing of cells by perfusion culturing of a cell culture comprising cell culture medium and cells, wherein cell culture medium is added to the cell culture, wherein the cell culture is circulated over a filter module comprising hollow fibers resulting in an outflow of liquid having a lower cell density than the cell culture and wherein the flow within the filter module is an alternating tangential flow.

It has surprisingly been found that by perfusion culturing of animal, in particular mammalian, cells or yeast cells according to the invention, extremely high viable cell densities can be obtained, whereas the cell culture further displays an extremely high cell viability. Furthermore, it was found that the perfusion process of the invention leads to less cell aggregation in the culture, and even to a culture being a suspension of single cells without visible aggregates. This is a surprising finding because the use of low shear conditions, such as in perfusion cell culturing, typically does not lead to disaggregation of cells. Cell aggregation during perfusion cell culturing is disadvantageous, because process control is more difficult, due to, for example, the heterogeneity in metabolic profiles of cells within the cell aggregates. This is especially troublesome if cells form aggregates of 5 cells or more and when the aggregates comprise in total 5% or more of the total amount of cells.

A perfusion process is described in U.S. Pat. No. 6,544,424. Although this document mentions that this process may be used for perfusion culturing of animal cells, it does neither disclose nor suggest the extremely high cell densities found in the present invention. Furthermore, U.S. Pat. No. 6,544,424 B1 discloses that the perfusion process could diminish the attachment and growth of an obstruction on the membrane surface of the hollow fibers, but it does neither disclose nor suggest that cells in the cell culture itself would aggregate less.

Voisier et al. (Biotechnol. Bioeng. 82 (2003), 751-765) review various cell retention techniques in high-density perfusion culture of suspended mammalian cells. None of the reviewed cell retention systems is able to provide the extremely high viable cell densities combined with the extremely high cell viability, of the present invention.

Perfusion culturing of cells has its conventional meaning in the art, i.e. it means that during culturing cells are retained by a separation device in which there is an outflow of liquid having a lower cell density than prior to separation and in which there is an inflow of the cell culture medium. In the process of the present invention, the separation device is a filter module comprising hollow fibers.

Perfusion culturing includes, but is not limited to continuous flow and semi-continuous flow, for example step-wise flow or staggered flow.

With the term "hollow fiber" is meant a tubular membrane. The internal diameter of the tube is preferably between 0.3 and 6.0 mm, more preferably between 0.5 and 3.0 mm, most preferably between 0.5 and 2.0 mm. Preferably, the mesh size in the membrane is chosen such that the size of the pores in the mesh is close to the diameter of the cells, ensuring a high retention of cells while cell debris can pass the filter. Preferably, the mesh size is between 3-30 µm.

Filter modules comprising hollow fibers are commercially available from for example General Electric (formerly Amersham).

With "alternating tangential flow within the filter module" is meant that there is one flow in the same direction as (i.e. tangential to) the membrane surfaces of the hollow fibers, which flow is going back and forth, and that there is another flow in a direction substantially perpendicular to said filter surface. Tangential flow can be achieved according to methods known to the person skilled in the art. For example, in U.S. Pat. No. 6,544,424 it is described that alternating tangential flow can be achieved using one pump to circulate the cell culture over a filter module comprising hollow fibers and another pump to remove the liquid having a lower cell density than prior to the filter separation.

In the process of the invention, any type of cell culture medium suitable for the culturing of cells can in principle be used. Guidelines for choosing a cell culture medium and cell culture conditions are well known in the art and are for instance provided in Chapter 8 and 9 of Freshney, R. I. Culture of animal cells (a manual of basic techniques), 4th edition 2000, Wiley-Liss and in Doyle, A., Griffiths, J. B., Newell, D. G. Cell &Tissue culture: Laboratory Procedures 1993, John Wiley & Sons.

Generally, a cell culture medium for mammalian cells comprises salts, amino acids, vitamins, lipids, detergents, buffers, growth factors, hormones, cytokines, trace elements and carbohydrates. Examples of salts include magnesium salts, for example $MgCl_2.6H_2O$, $MgSO_4$ and $MgSO_4.7H_2O$ iron salts, for example $FeSO_4.7H_2O$, potassium salts, for example $KH_2PO_4$, KCl; sodium salts, for example $NaH_2PO_4$, $Na_2HPO_4$ and calcium salts, for example $CaCl_2.2H_2O$. Examples of amino acids are all 20 known proteinogenic amino acids, for example hystidine, glutamine, threonine, serine, methionine. Examples of vitamins include: ascorbate, biotin, choline.Cl, myo-inositol, D-panthothenate, riboflavin. Examples of lipids include: fatty acids, for example linoleic acid and oleic acid; soy peptone and ethanol amine. Examples of detergents include Tween 80 and Pluronic F68. An example of a buffer is HEPES. Examples of growth factors/hormones/cytokines include IGF, hydrocortisone and (recombinant) insulin. Examples of trace elements are known to the person skilled in the art and include Zn, Mg and Se. Examples of carbohydrates include glucose, fructose, galactose and pyruvate.

The pH, temperature, dissolved oxygen concentration and osmolarity of the cell culture medium are in principle not critical and depend on the type of cell chosen. Preferably, the pH, temperature, dissolved oxygen concentration and osmolarity are chosen such that it is optimal for the growth and productivity of the cells. The person skilled in the art knows how to find the optimal pH, temperature, dissolved oxygen concentration and osmolarity for the perfusion culturing. Usually, the optimal pH is between 6.6 and 7.6, the optimal temperature between 30 and 39° C., the optimal osmolarity between 260 and 400 mOsm/kg.

Cells that are advantageously subjected to the process of the invention may be any cell type benefiting from this process, i.e. culturing to an extremely high viable cell density and an extremely high cell viability.

According to the process of the invention, an extremely high viable cell density is a density of at least $80 \times 10^6$ cells per mL, preferably at least $100 \times 10^6$ cells per mL, more preferably at least $110 \times 10^6$ cells per mL, more preferably at least $120 \times 10^6$ cells per mL, more preferably at least $130 \times 10^6$ cells per mL, most preferably at least $140 \times 10^6$ cells per mL. Typically, a suitable upper limit in the cell density may lie around $500 \times 10^6$ cells per mL.

Surprisingly, the extremely high cell density of the process of the invention is accompanied by an extremely high cell viability. An extremely high cell viability is a viability of at least 90%, preferably at least 95%, more preferably at least 97%, most preferably at least 99%.

It is to be understood that the very high viable cell density and very high cell viability are reached after a certain period of perfusion culturing, generally when the cells have reached a steady state, for mammalian cells typically 12 to 25 days after the initiation of perfusion culturing.

The process of the invention is suitable for culturing animal cells or yeast cells, especially for culturing mammalian cells.

The process of the invention is further especially suitable for culturing cells that easily or inherently form aggregates during culturing, especially during perfusion culturing (so-called aggregating cells). Surprisingly, the process of the invention not only diminishes aggregate disposal on the filter membrane, but also diminishes aggregation of cells during the perfusion culture process, even aggregation of cells with an inherent tendency to form aggregates. The culturing of aggregating cells according to the invention results in a culture wherein aggregates of at least 5 cells comprise at the most 5% of the total amount of cells, preferably at the most 4%, more preferably at the most 3%, even more preferably at the most 2% of the total amount of cells. Especially preferably, the culturing of aggregating cells according to the invention results in a culture that is a real single cell suspension.

Aggregating cells are cells that form aggregates of at least 5 cells, the aggregates comprising in total at least 5% of the total amount of cells. Preferably, the aggregates consist of at least 6, more preferably at least 7, even more preferably at least 8, even more preferably at least 9, even more preferably at least 10 cells. Preferably, the aggregates comprise in total at least 7%, more preferably at least 10%, most preferably at least 15% of the total amount of cells.

Examples of mammalian cells include: CHO (Chinese Hamster Ovary) cells, hybridomas, BHK (Baby Hamster Kidney) cells, myeloma cells, human cells, for example HEK-293 cells, human lymphoblastoid cells, PER.C6® cells, mouse cells, for example NS0 cells. Examples of yeast cells include *Saccharomyces cerevisiae, Phaffia rhodozyma, Kluyveromyces lactis*, or yeast cells from the genus *Pichia*.

Preferably, mammalian cells are used, more preferably CHO, NS0, PER.C6® cells. Also preferably, cells known for their aggregating behaviour during culturing (aggregating cells) are used. Most preferably, PER.C6® cells are used.

Cell aggregation may for example be determined under a microscope.

The rate of addition of cell culture medium to the culture (the inflow rate or perfusion rate) influences the viability and the density of the cells.

In one embodiment of the invention, the cell culture medium is added at a perfusion rate according to the following formula 1:

$$\text{Perfusion rate} = \text{SPR} * \text{total cell culture volume} * \text{viable cell density} \qquad (1)$$

wherein the perfusion rate is expressed in liters per day, wherein the SPR is the specific perfusion rate, i.e. the rate in which the cell culture medium is fed to the cell culture expressed as the volume of medium added per viable cell per time unit and wherein the viable cell density is the number of viable cells per unit of volume. The number of viable cells can be determined by the person skilled in the art, for example via the trypan blue exclusion method.

The specific perfusion rate is preferably chosen between 0.01 and 0.3 nL/cell/day, more preferably between 0.01 and 0.2 nL/cell/day.

It may be of advantage to take into account additional parameters when adjusting the perfusion rate, for example the amount of glucose to be fed to the culture and/or the oxygen concentration. For example, for PER.C6® the glucose perfusion rate is preferably chosen between 3 and 20 mmoles/L, more preferably between 5 and 15 mmoles/L, as part of the medium perfusion rate.

A person skilled in the art knows how to determine the outflow rate. The outflow rate of the liquid is determined by the perfusion rate and is generally chosen at an equal value.

In one embodiment of the invention, the outflow liquid is substantially devoid of viable cells.

In another embodiment of the invention, biomass (i.e. cells in cell culture) is removed at least once from the cell culture and additional cell culture medium is added to the cell culture to compensate for the biomass removal. Biomass removal may lead to higher cell densities. Biomass may be removed continuously or step-wise.

In the step-wise approach, biomass is removed continuously for a defined time period. If a step-wise approach is used, biomass removal is preferably started just before or just after the cells have reached a steady state.

If a step-wise approach is used, a volume of biomass of preferably between 2 and 40% of the working volume per day, more preferably between 5 and 30% of the working volume per day, even more preferably between 10 and 25% of the working volume per day is removed per biomass removal step.

With "working volume" is meant the total volume of the cell culture.

With "biomass removal step" is meant the time from the start to the stop of the biomass removal. If a continuous approach is used, the biomass is removed continuously until the end of the cell culturing. Preferably, the continuous removal of biomass is started just before or just after the cells have reached a steady state. Preferably, a volume of biomass is removed of between 2 and 40% of the working volume per day, more preferably between 3 and 30% of the working volume per day, even more preferably between 4 and 15% of the working volume per day.

The addition of the additional cell culture medium is done to compensate for the biomass removal. The feed wherein additional cell culture medium is added to the cell culture may be merged into the perfusion feed, but may also be added in a separate feed. The person skilled in the art is aware how much additional cell culture medium is needed to compensate for the biomass removal. Generally, the rate of addition of the additional cell culture medium to the cell culture will be the same as the biomass removal rate.

In yet another embodiment of the invention, a biological substance is produced by the cells. The biological substances that can suitably be produced in the perfusion culturing of the cell are in principle all biological substances that can be produced by animal, especially mammalian, and yeast cells, for example therapeutic and diagnostic proteins, such as monoclonal antibodies, growth factors or peptide hormones, enzymes, polynucleotides, such as viral vectors used in gene therapy, vaccines, etc.

In the perfusion culturing process of the invention, the outflow liquid will have a lower cell density but the same concentration of the biological substance than the liquid prior to separation.

Preferably, the process according to the invention is used for the production of a biopharmaceutical product, which is a biological substance with a medical application. Examples of biopharmaceutical products are as follows (with examples of brand names of the corresponding biopharmaceutical product between brackets): Tenecteplase (TN Kase™), (recombinant) antihemophilic factor (ReFacto™) lymphoblastoid Interferon α-n1 (Wellferon™), (recombinant) Coagulation factor (NovoSeven™), Etanercept, (Enbrel™), Trastuzumab (Herceptin™), Infliximab (Remicade™), Basiliximab (Simulect™), Daclizumab (Zenapaz™), (recombinant) Coagulation factor IX (Benefix™), erythropoietin alpha (Epogen®), G-CSF (Neupogen®Filgrastim), Interferon alpha-2b (Infergen®), recombinant insulin (Humulin®), Interferon beta 1a (Avonex®), Factor VIII (KoGENate®), Glucocerebrosidase (Cerezyme™), Interferon beta 1b (Betaseron®), TNF alpha receptor (Enbrel®), Follicle stimulating hormone (Gonal-F®), Mab abcixmab (Synagis®, ReoPro®), Mab ritiximab (Rituxan®), tissue plasminogen activator (Activase®, Actilyase®), human growth hormone (Protropin®, Norditropin®, GenoTropin™). Examples of polynucleotides with a possible medical application are gene therapeutic plasmid DNAs. Some gene therapeutic DNAs are presently tested in clinical trials for their medical application. Examples of vaccines are live, oral, tetravalent Rotavirus vaccine (RotaShield™), rabies vaccine (RanAvert™), Hepatitis B vaccin (RECOMBIVAX HB®, Engerix®) and inactivated hepatitis A vaccine (VAQTA™).

The biological substance in the outflow may be further purified in so-called downstream processing. Downstream processing usually comprises several purification steps in varying combinations and order. Examples of purification steps in the downstream processing are separation steps (e.g. by affinity chromatography and/or ion exchange chromatography), steps for the concentration of the biological substance (e.g. by ultrafiltration or diafiltration), steps to exchange buffers and/or steps to remove or inactivate viruses (e.g. by virus-filtration, pH shift or solvent detergent treatment).

The invention will now be elucidated by way of the following examples, without however being limited thereto.

EXAMPLE 1

Process Optimisation of the Human Cell Line PER.C6® for the Production of Biopharmaceuticals Introduction A number of expression platforms now exist for the production of biopharmaceuticals. Most of the new products must choose a mammalian system due in main part to the glycosylation machinery which these cells contain and others lack. However to date the cell mass and resulting productivity of these cells is a factor of 10-100 times less than a corresponding microbial system if these cells had the machinery to make such products.

A perfusion culture setup was developed for the PER.C6® cell line, a human cell line that possesses a number of features that makes it favourable for the production of biopharmaceuticals. A perfusion setup involves the separation of various components of the culture broth so that cells are retained, harvest is captured and medium refreshment occurs. The performance of a spinfilter, an acoustic device and an alternating tangential flow unit within a continuous perfusion culture of the PER.C6® cell line was assessed.

Materials & Methods

Cell Line and Maintenance: A PER.C6® cell line was used in this study that produces a human IgG. Cells were maintained in a serum free commercial medium (EX-CELL™ VPRO medium, JRH Biosciences), supplemented with 6 mM L-glutamine (Gibco). The PER.C6® cell line is a human embryonic cell-line immortalised with adenovirus type-5 (ad5) E1 gene using a phosphoglyceratekinase promoter.

Bioreactor Set-Up: 1 L and 4 L working volume reactors (Applikon, Netherlands and B.Braun, Germany) were used during this study. A Braun DCU3 controller (B.Braun, Germany) was used to operate the process at defined setpoints. Temperature was maintained at 36.5° C. (range 35.5-37.5° C.). Dissolved oxygen concentration was controlled at 50% (range 40-60%) of air saturation by automatic adjustment of inlet gas composition through the headspace and intermittent sparging through a microporous sparger. The pH setpoint was 7.1 (range 6.7-7.5) and controlled by the flow of $CO_2$ via the headspace. Cells were inoculated in the fermenter with an inoculum viable cell density range of $0.2$-$0.5*10^6$ cells/mL. Perfusion started at a viable cell density in the range of $1$-$3*10^6$ cells/mL.

Cell Retention: Cells were retained in the reactor using three different devices. First a spinfilter with a 10 μm pore size (GKD, Düren Germany) was used. Secondly, a Biosep ADI1015 cell retention system and controller (AppliSens, the Netherlands) was used. Finally an ATF™-4 control unit and housing with associate hollow fiber membrane module (Refine Technology, USA) was assessed. The hollow fiber filter used was model CFP-2-E-8SIP (0.2 micron, Area: 4600 $cm^2$, Amersham Bioscience obtained from Magellan instruments, USA). To maintain a constant culture volume a level sensor control loop was in operation.

Analytical Methods: A cell count from the bioreactor was performed using the trypan blue exclusion method. The number of viable cells was determined as follows: An amount of cells stained with trypan blue was transferred to a Fuchs Rosenthal haemacytometer. The chamber of the haemacytometer was placed under a microscope and an appropriate number of boxes was counted. The viable cell density was calculated using the following formula:

$$\text{Viable cell density}(X10^5 \text{ cells/ml}) = (A+B) \times E/320 \quad (2)$$

Wherein
A=number of non-stained cells in square A
B=number of non-stained cells in square B
E=dilution factor Antibody concentration was determined by a analytical protein A column using a HPLC with UV280 nm absorption detection; the actual concentration was determined on basis of a calibration curve of a IgG1 reference standard.

Results

Perfusion Cultures

Results obtained with the above materials and methods are shown in FIGS. 1-6.

Summary

See Table 1 for an overview of the data obtained for the different types of perfusion.

TABLE 1

Overview of the viable cell density, volumetric production rate (based on reactor volume) and the yield improvement of the perfusion runs using the three different retention devices.
Batch and fed-batch results are added for comparison (data not shown).

| Process | Max. Viable Cell Density ($10^6$ cells/mL) | Productivity | Yield (total amount of product produced) Improvement Factor |
|---|---|---|---|
| Batch | 8-10 | 0.5 g/L | 1 |
| Fed-Batch | 8-10 | 1.2 g/L | 2.4 |
| Continuous Perfusion | | | |
| Spin filter retention device | 20-30 | 0.1-0.2 g/L/day | 2.8-5.6 |
| Acoustic retention device | 20 | 0.6 g/L/day | 16.8 |
| Alternating tangential flow retention device | 100 | 0.9 g/L/day | 25.2 |

It can be concluded that continuous perfusion experiments using the alternating tangential flow unit show significant potential to achieve very high cell densities and product concentrations ($100 \times 10^6$ cells/mL and 0.9 g/L/day), while no aggregation of the PER.C6® cells was observed.

EXAMPLE 2

Culturing of PER.C6® Cells by Perfusion

Equipment: B.Braun fermenter control unit (Braun, Germany), 7 L Braun vessel and headplate with associated pH, dissolved oxygen (DO) and level sensor probes (Braun, Germany), ATF™-4 control unit and housing with associate hollow fiber membrane module (Refine Technology, USA).
Filter
Filter model: CFP-2-E-8SIP
Type: 0.2 micron
Area: 4600 cm$^2$
Amersham Bioscience Working Volume
Setpoint: 4.1 L
Range: 3.8-4.7 L

| Alternating tangential flow settings | | |
|---|---|---|
| Parameter | Setpoint | Range |
| Pressure rising setpoint (psi) | Variable | 2-4 |
| Pressure rising flow (L/min) | 3.2 | 2.5-4.0 |
| Exhaust flow (L/min) | 3.2 | 2.5-4.0 |
| Exhaust time (s) | Variable | 3-8 |
| Pre-pressure (psi) | Variable | 5-9 |

Bleed Rate

No biomass removal was applied to this process.

Materials:

6 mM (final volume) L-glutamine (Gibco) in Ex-CELL™ VPRO medium (JRH Bioscience, USA), 12% $Na_2CO_3$ is used to control the pH.

Cell Lines and Culture Conditions

A PER.C6® cell line expressing a model IgG was investigated in this study. The PER.C6® cell line is generated from retina-derived primary human cells. The PER.C6® cell line is able to generate complete human monoclonal antibodies (including the glycans) (ref 1, ref 2).

Cells were cultured in shaking Erlenymer flasks at 110 rpm and 36.5° C. The headspace of these flasks was controlled using a mixture of 5% $CO_2$/Air.

Ref 1: Jones, D. H., van Berkel, P. H. C., Logtenberg, T. and Bout, A., 2002, 'PER.C6 cell line for human antibody production', Gen. Eng. News 22, 50-54.

Ref 2: Jones, D. et al., 2003, 'High-level expression of recombinant IgG in the human cell line PER.C6', Biotechnol. Prog. 19, 163-168.

Operation of Fermenter

Cells were cultured in a fermenter where dissolved oxygen tension, pH, temperature and agitation rate were controlled as detailed below.

| Parameter | Setpoint | Range |
|---|---|---|
| Temperature | 36.5° C. | 35.5-37.5 |
| pH | >6.7 | 7.5-6.7 |
| | | Active pH control using 12% $Na_2CO_3$ if pH<6.7 |
| DO | 50% | 40-60% |
| Agitation | 100-300 | Staged increase as viable cell density (VCD) increases; |

| VCD ($\times 10^6$ cells/ml) | Agitation (rpm) |
|---|---|
| 0.3-10 | 120 |
| 10-30 | 150 |
| 30-50 | 170 |
| 50-80 | 200 |
| 80-100 | 230 |
| 100-120 | 260 |
| >120 | 300 |

Process Description:

Cells are inoculated in a fermenter with an inoculation viable cell density range of $0.2-0.5 \times 10^6$ cells/ml and a setpoint of $0.3 \times 10^6$ cells/ml. Perfusion is begun when the viable cell density $>2 \times 10^6$ cells/ml or at day 5 of the culture whichever is achieved first.

The perfusion rate is dependent on the cell density of the culture and the rates used are described in the table below.

Both the flow rate and the dilution rate are adjusted as the cell density in the fermenter increases.

Perfusion Rates Utilized for Culture of PER.C6® Cells

| Viable cell density (×10⁶ cells/ml) | Specific perfusion rate (nl/cell/day) | Setpoint of specific perfusion rate (nl/cell/day) |
|---|---|---|
| Day 1 of perfusion | 0.15-0.25 | 0.2 |
| 3-50 | 0.03-0.06 | 0.04 |
| 50-80 | 0.025-0.035 | 0.03 |
| >80 | 0.01-0.03 | 0.02 |

Figure 1:
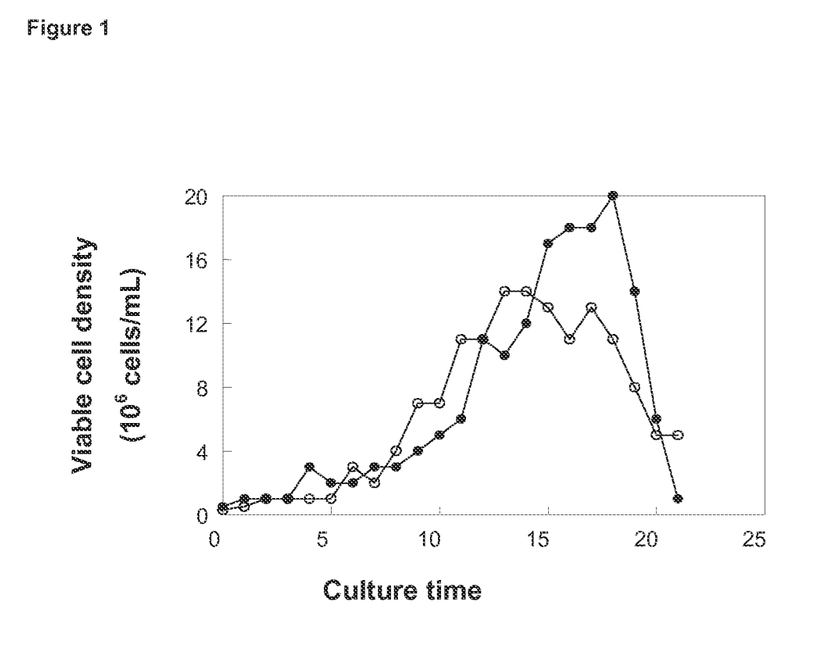
FIG. 1: Viable cell density ($\times 10^6$ cells/ml) versus culture time (days) for two different continuous perfusion fermentations of an IgG1 producing PER.C6® clone using a spinfilter separation device. Stirrer speed setting of the 1 L Applikon fermenter was 100-150 rpm. The perfusion runs were performed in 1 L working volume. The specific perfusion rate (SPR) for both perfusion runs was 0.1-0.3 mL/cell/day. In both cases the perfusion runs had to be terminated because of spin filter clogging.
Figure 2:
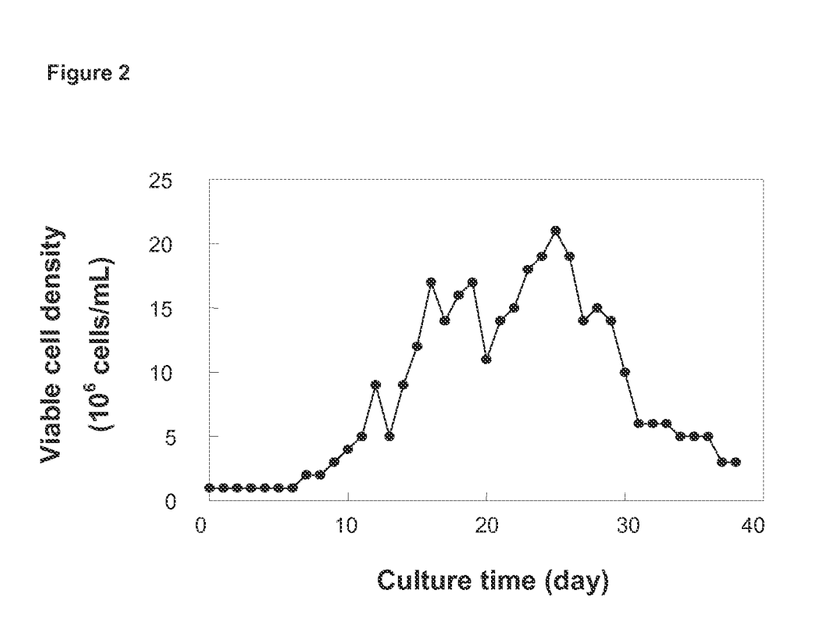
FIG. 2: Growth of IgG1 producing PER.C6® cells in a continuous perfusion system with an acoustic device as a cell retention system. Stirrer speed setting of the 1 L Applikon fermenter was 100-150 rpm. The settings used for the run/stop cycle were 300 s forward and 4.5 s backwards. During the run this was adapted to a 300 s/3 s cycle (day 15). The specific perfusion rate (SPR) for the perfusion run was between 0.1-0.3 nL/cell/day.
Figure 3:
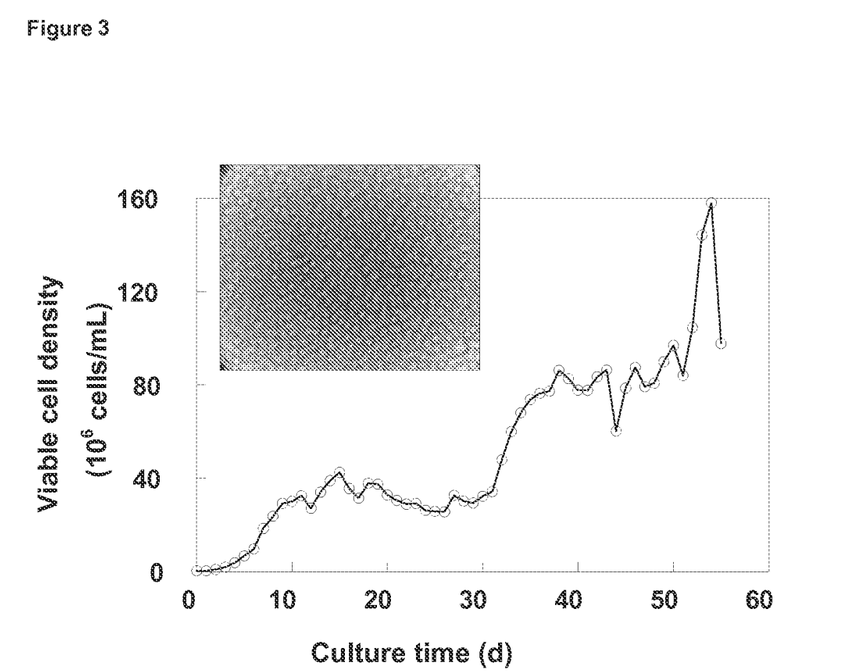
FIG. 3: Growth of IgG1 producing PER.C6® cells in a continuous perfusion system with an ATF™-4 unit as a cell retention system. The experiment was performed in a 4 L Applikon fermenter. Setting for the stirrer speed was 125 rpm. The ATF-4 operated between 0.5 and 3 working volumes per day. The SPR was set at 0.03-0.08 nL/cell/day. The inset shows the high cell density of the culture, being completely devoid of aggregating cells.
Figure 4:
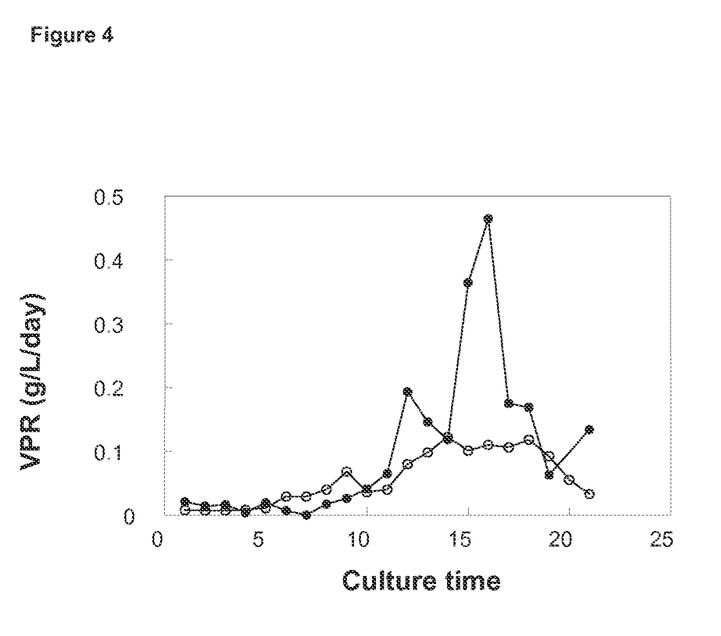
FIG. 4: Productivity of IgG1 versus culture time (days) for two different continuous perfusion fermentations of a IgG1 producing PER.C6® clone using a spinfilter separation device.
Figure 5:
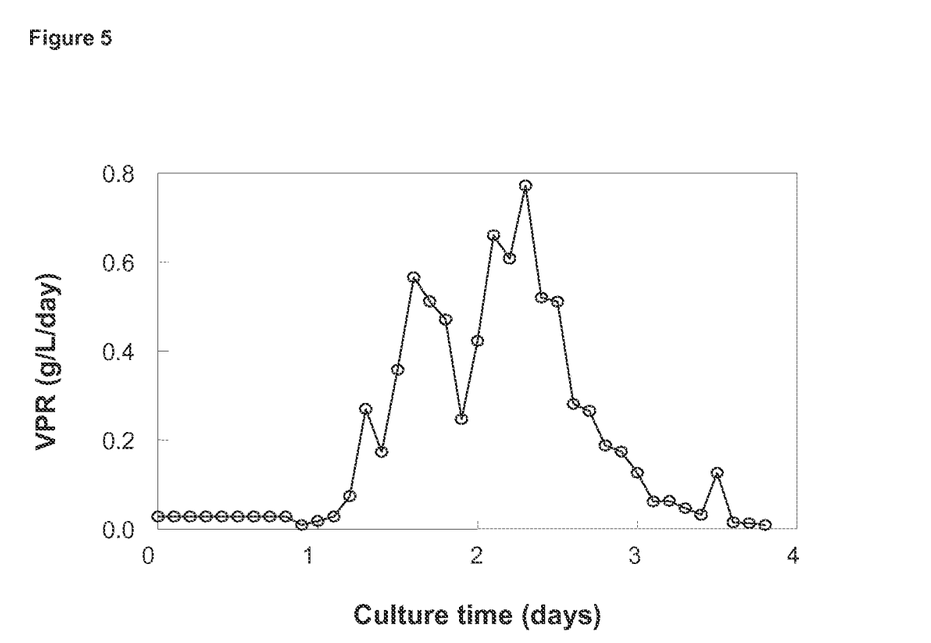
FIG. 5: Productivity of IgG1 producing PER.C6™ cells in a continuous perfusion system with an acoustic device as a cell retention system.
Figure 6:
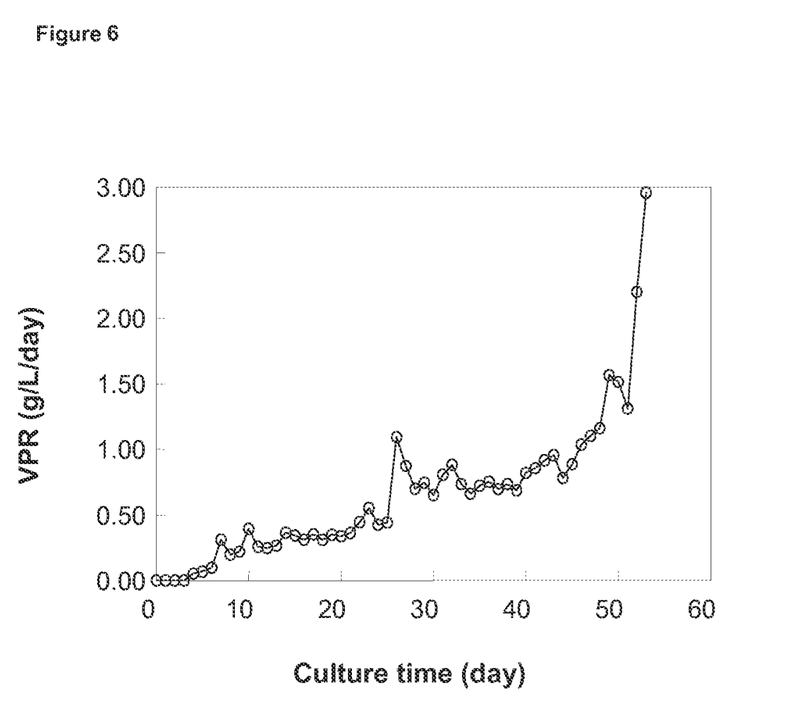
FIG. 6: Productivity of IgG1 producing PER.C6® cells in a continuous perfusion system with an alternating tangential flow unit as a cell retention system.
Figure 7:
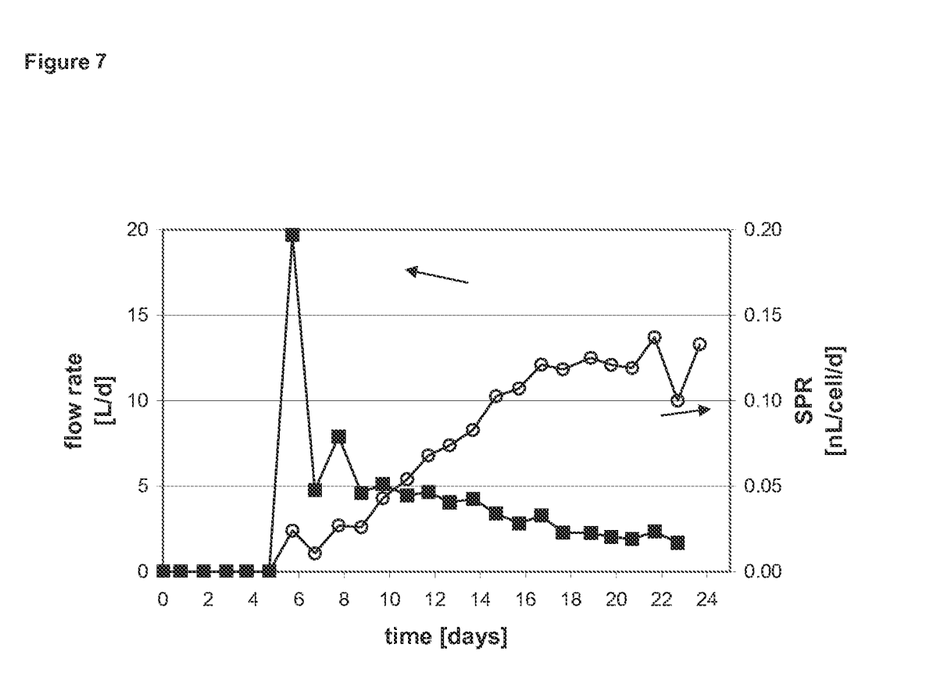
FIG. 7: Culture time (days) versus flow (L/day) and specific perfusion rate (SPR in nl/cell/day) for PER.C6® cells cultured using a perfusion process.
Figure 8:
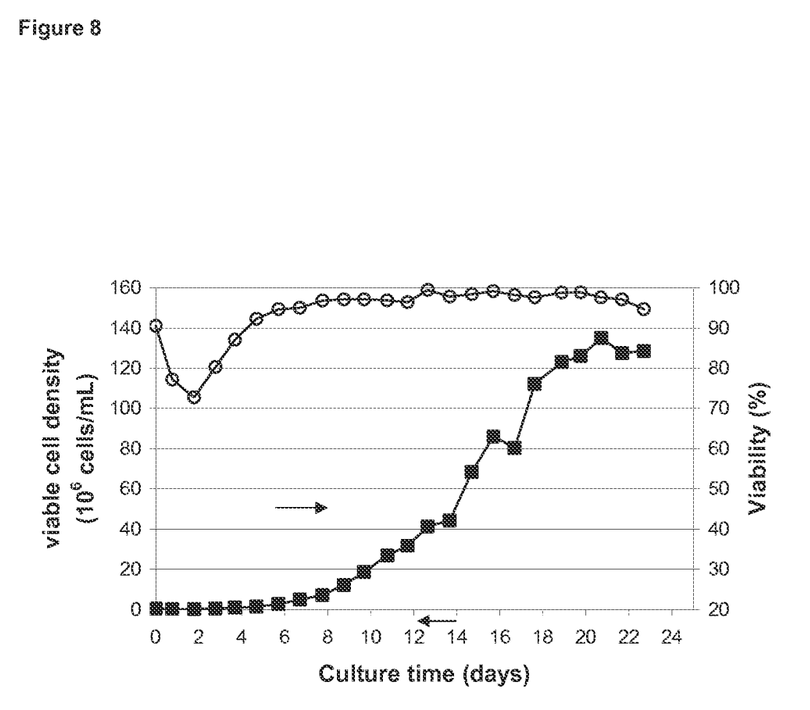
FIG. 8: Viable cell density and cell viability using the procedure described in example 2.

The actual data and results from this example (amongst others flow rates and specific perfusion rates used in this example) are shown in Table 2 below and in FIGS. 7 and 8.

TABLE 2

Raw data obtained for example 2

| Time day | flow rate (FR) L/day | dilution rate (D) working volume/day | Specific perfusion rate (SPR) nL/cell · day | Viable count (VC) 10⁶/mL | Viability % | product concentration g/L | Specific production rate of IgG1 pg/(cell · day) | Volumetric production rate g/L · day |
|---|---|---|---|---|---|---|---|---|
| 0 | 0.00 | 0.00 | 0.00 | 0.6 | 90 | 0.012 | NA | NA |
| 1 | 0.00 | 0.00 | 0.00 | 0.3 | 77 | 0.008 | NA | 0.000 |
| 2 | 0.00 | 0.00 | 0.00 | 0.3 | 73 | 0.008 | 0.0 | 0.000 |
| 3 | 0.00 | 0.00 | 0.00 | 0.5 | 80 | 0.013 | 12.1 | 0.000 |
| 4 | 0.00 | 0.00 | 0.00 | 0.9 | 87 | 0.019 | 9.3 | 0.000 |
| 5 | 0.00 | 0.00 | 0.00 | 1.4 | 92 | 0.033 | 12.0 | 0.000 |
| 6 | 2.39 | 0.52 | 0.20 | 2.6 | 95 | 0.035 | 5.5 | 0.009 |
| 7 | 1.06 | 0.24 | 0.05 | 4.9 | 95 | 0.054 | 9.5 | 0.017 |
| 8 | 2.70 | 0.57 | 0.08 | 7.3 | 97 | 0.073 | 7.2 | 0.026 |
| 9 | 2.60 | 0.57 | 0.05 | 12.3 | 97 | 0.067 | 3.5 | 0.040 |
| 10 | 4.29 | 0.95 | 0.05 | 18.6 | 97 | 0.115 | 7.8 | 0.069 |
| 11 | 5.40 | 1.20 | 0.04 | 26.9 | 97 | 0.140 | 7.0 | 0.137 |
| 12 | 6.80 | 1.48 | 0.05 | 31.8 | 96 | 0.127 | 5.6 | 0.179 |
| 13 | 7.39 | 1.68 | 0.04 | 41.4 | 99 | 0.129 | 5.6 | 0.202 |
| 14 | 8.28 | 1.88 | 0.04 | 44.3 | 98 | 0.139 | 5.8 | 0.238 |
| 15 | 10.26 | 2.33 | 0.03 | 68.3 | 98 | 0.116 | 4.4 | 0.269 |
| 16 | 10.70 | 2.43 | 0.03 | 86.1 | 99 | 0.151 | 4.6 | 0.318 |
| 17 | 12.10 | 2.63 | 0.03 | 80.3 | 98 | 0.163 | 4.9 | 0.397 |
| 18 | 11.83 | 2.57 | 0.02 | 112.3 | 98 | 0.292 | 7.6 | 0.592 |
| 19 | 12.50 | 2.78 | 0.02 | 123.0 | 99 | 0.291 | 6.6 | 0.780 |
| 20 | 12.09 | 2.57 | 0.02 | 126.0 | 99 | 0.293 | 6.3 | 0.781 |
| 21 | 11.91 | 2.59 | 0.02 | 135.0 | 98 | 0.332 | 6.5 | 0.806 |
| 22 | 13.70 | 2.98 | 0.02 | 127.5 | 97 | 0.395 | 8.2 | 1.012 |
| 23 | 10.00 | 2.17 | 0.02 | 128.5 | 95 | 0.470 | 9.3 | 1.114 |

The invention claimed is:

1. A method for limiting cell aggregation during cell culture to a level wherein no more than 5% of the animal cells in suspension in the culture comprise aggregates of at least 5 cells, comprising:

culturing of a cell culture comprising cell culture medium and animal cells that easily or inherently form aggregates during culturing, wherein the culturing comprises:

(a) circulating the cell culture through a filter module comprising hollow fibers, in an alternating tangential flow resulting in an outflow of cell culture liquid through the pores of the filter module having a lower animal cell density per ml than the cell culture prior to circulating through the filter module; and (b) adding cell culture medium to the cell culture, and wherein no more than 5% of the animal cells in the culture form aggregates in suspension of at least 5 cells during the culturing, and wherein the culturing is continued until animal cells are present in the cell culture at a density of at least 80×10⁶ viable animal cells/ml.

2. The method of claim 1, wherein biomass is removed at least once from the cell culture and additional cell culture medium is added to the cell culture to compensate for the biomass removal.

3. The method of claim 2, wherein the biomass removal is started just before or just after the animal cell density has reached a steady state.

4. The method of claim 2, wherein the volume of biomass removed is between 2% and 40% of the total volume of the cell culture per day.

5. The method of claim 1, wherein a first pump circulates the cell culture within the filter module comprising hollow fibers and a second pump removes the liquid having a lower cell density than the cell culture prior to circulating through the filter module.

6. The method of claim 1, wherein the animal cells are cultured to a cell viability of at least 90%.

7. The method of claim 1, wherein no more than 4% of the animal cells in the culture form aggregates in suspension of at least 5 cells during the culturing.

8. The method of claim 1, wherein the cells are mammalian cells.

9. The method of claim 8, wherein the mammalian cells are human cells.

10. The method of claim 1, wherein the cells produce a biological substance.

11. The method of claim 10, wherein the biological substance is a protein or a polynucleotide.

12. The method of claim 10, wherein the biological substance is further purified from the cell culture in downstream processing.

13. The method of claim 3, wherein the cells are mammalian cells.

14. The method of claim 13, wherein the mammalian cells are human cells.

15. The method of claim 13, wherein the cells produce a biological substance.

16. The method of claim 15, wherein the biological substance is a protein or a polynucleotide.

17. The method of claim 15, wherein the biological substance is further purified from the cell culture in downstream processing.

18. The method of claim 14, wherein the cells produce a biological substance.

19. The method of claim 18, wherein the biological substance is a protein or a polynucleotide.

20. The method of claim 18, wherein the biological substance is further purified from the cell culture in downstream processing.

* * * * *